US006582414B1

(12) United States Patent
Richardson

(10) Patent No.: US 6,582,414 B1
(45) Date of Patent: Jun. 24, 2003

(54) DISPOSABLE GARMENT HAVING IMPROVED FITNESS TO BODY DURING USE

(75) Inventor: James William Richardson, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,045

(22) PCT Filed: Mar. 26, 1998

(86) PCT No.: PCT/US98/05904
§ 371 (c)(1),
(2), (4) Date: Sep. 25, 2000

(87) PCT Pub. No.: WO99/48452
PCT Pub. Date: Sep. 30, 1999

(51) Int. Cl.⁷ .................................................. A61F 13/15
(52) U.S. Cl. ................................. 604/385.24; 604/396
(58) Field of Search ............................ 604/396, 385.01, 604/385.16, 385.22, 385.24, 385.27

(56) References Cited

U.S. PATENT DOCUMENTS

| | | | | |
|---|---|---|---|---|
| 3,658,064 A | * | 4/1972 | Pociluyko | 128/287 |
| 4,938,757 A | * | 7/1990 | Van Gompell et al. | 604/396 |
| 4,940,464 A | | 7/1990 | Van Gompel et al. | |
| 5,569,234 A | | 10/1996 | Buell et al. | |
| 5,685,873 A | * | 11/1997 | Bruemmer et al. | 604/385.2 |
| 5,769,838 A | * | 6/1998 | Buell et al. | 604/396 |
| 5,807,368 A | * | 9/1998 | Helmer | 604/373 |
| 5,836,932 A | * | 11/1998 | Buell et al. | 604/396 |
| 5,993,431 A | * | 11/1999 | McFall et al. | 604/385.2 |
| 6,090,994 A | * | 7/2000 | Chen | 604/378 |
| 6,179,820 B1 | * | 1/2001 | Ferfors | 604/385.27 |
| 6,213,991 B1 | * | 4/2001 | Kling et al. | 604/385.01 |
| 6,264,642 B1 | * | 7/2001 | Kuen et al. | 604/385.28 |
| 6,297,424 B1 | * | 10/2001 | Olson et al. | 604/361 |
| 6,307,119 B1 | * | 10/2001 | Cammarota et al. | 604/361 |
| 6,325,787 B1 | * | 12/2001 | Roe et al. | 604/385.27 |
| 6,375,646 B1 | * | 4/2002 | Widlund et al. | 604/385.3 |
| 6,534,694 | * | 3/2003 | Kling et al. | 604/366 |

FOREIGN PATENT DOCUMENTS

GB    2 268 389 A    1/1994

* cited by examiner

Primary Examiner—Weilun Lo
Assistant Examiner—Michael Bogart
(74) Attorney, Agent, or Firm—Michael P. Hayden; David M. Weirich; Ken K. Patel

(57) ABSTRACT

A disposable garment comprising a chassis having a front region, a back region, and a crotch region between the front and back regions, the chassis comprising a liquid impervious backsheet and at least one pair of side panels extending laterally outwardly from the chassis. The backsheet comprises a liquid impervious film extending longitudinally in the front, back, and crotch regions, and having a nonuniform lateral width so as to form a first portion in the crotch region and a second portion in the front or back region. The second portion has a lateral width dimension less than the lateral width dimension of the first portion such that the film does not extend into the side panels. At least one of the side panels comprises an elastomeric material extending laterally outwardly from the chassis, wherein the elastomeric material is joined to the second portion of the liquid impervious film.

9 Claims, 6 Drawing Sheets

DISPOSABLE GARMENT HAVING IMPROVED FITNESS TO BODY DURING USE

FIELD

The present invention relates to disposable garments. Examples of such disposable garments include disposable underwear, disposable diapers including pull-on diapers and training pants, and disposable panties for menstrual use. More specifically, the present invention relates to disposable garments which have improved fitness to body during use.

BACKGROUND

Infants and other incontinent individuals wear disposable garments such as diapers to receive and contain urine and other body exudes. One type of the disposable garments, which is often called as "tape type", has a fastener system to hold the disposable garment at the wearer's waist area. As the fastener system, either an adhesive tape system or a mechanical fastener system is often used. Recently, elastically stretchable side panels are preferably used in this type of the disposable garments, because they can provide a better fit to the wearer's waist area by jointly working with the fastener system. Another type of absorbent garments, which is often called as "pant type" or "pull-on", has fixed sides has become popular for use on children able to walk and often who are toilet training. The pull-on garments have side panels which edges are seamed together to form two leg openings and a waist opening. These pull-on garments need to fit snugly about the waist and legs of the wearer without drooping, sagging or sliding down from its position on the torso to contain body exudes. Examples of these pull-on garments are disclosed, for example, in U.S. Pat No. 5,171,239 to lgaue et al., U.S. Pat No. 4,610,681 to Strohbeen et al., WO 93/17648 published on Sep. 16, 1993, U.S. Pat No. 4,940,464 to Van Gompel et al., U.S. Pat. No. 5,246,433 to Hasse et al., and U.S. Pat No. 5,569,234 to Buell et al.

These disposable garments have stretch laminates in the side panels to provide a better fitness of the garments on the wearer. The stretch laminates usually have an elastic material which has important factors for the fitness of disposable garments. More specifically, the extension properties including the extension forces, recovery forces, retention forces, and available stretch (extension) of the elastic material are important considerations in the performance of the fitness during use. They also effect the ability of the applicator to achieve a suitable degree of application stretch for pull-on garments.

In the meantime, disposable garments typically have a liquid impervious backsheet to prevent absorbed liquid from passing through the garment and soiling adjacent articles such as clothing, bedding and the like. It is generally expected that the liquid impervious backsheet is flexible enough to be compliant and readily conformable to the general shape of the human body. However, depending on the structural relationship between the liquid impervious backsheet and the elastic material used in the side panels, the elastic material can not fully provide expected properties, resulting in loss of the performance of the fitness of disposable garments during use. Thus, none of the existing art provides all of the advantages and benefits of the present invention.

SUMMARY

The present invention is directed to a disposable garment, comprising a chassis having a longitudinal centerline, a front region, a back region and a crotch region between the front region and the back region, the chassis comprising a liquid pervious topsheet, a liquid impervious backsheet associated with the topsheet, and an absorbent core disposed between the topsheet and the backsheet; and at least one pair of side panels extending laterally outwardly from the chassis in the front or back region. The backsheet comprises a nonwoven outer cover and a liquid impervious film joined to the outer cover. The liquid impervious film longitudinally extends in the front, back and crotch regions, and has a nonuniform lateral width so as to form a first portion in at least a portion of the crotch region, and a second portion in at least a portion of the front or back region. The second portion has a lateral width dimension less than the lateral width dimension of the first portion such that the film does not extend into the at least one pair of side panels. At least one of the side panels comprises an elastomeric material extending laterally outwardly from the chassis, wherein the elastomeric material is joined to the second portion of the liquid impervious film.

These and other features, aspects, and advantages of the present invention will become evident to those skilled in the art from a reading of the present disclosure.

BRIEF DESCRIPTION OF THE DRAWINGS

While the specification concludes with claims particularly pointing out and distinctly claiming the invention, it is believed that the invention will be better a understood from the following description of preferred embodiments which is taken in conjunction with the accompanying drawings and which like designations are used to designate substantially identical elements, and in which:

DETAILED DESCRIPTION

All cited references are incorporated herein by reference in their entireties.

Citation of any reference is not an admission regarding any determination as to its availability as prior art to the claimed invention.

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the side panels are not separate elements joined to a separate chassis in that the side panels are formed by at least one layer which also forms the central panel or chassis of the garment (i.e., the garment does not require separately manipulative panels such as a separate chassis and separate side panels). The pull-on garment is also preferably "absorbent" to absorb and contain the various exudates discharged from the body. A preferred embodiment of the pull-on garment of the present invention is the unitary disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. As used herein, the term "panel" is used herein to denote an area or element of the pull-on garment. (While a panel is typically a distinct area or element, a panel may coincide (functionally correspond) somewhat with an adjacent panel.) As used herein, the term "joined" or "joining" encompasses configurations whereby an element is directly secured to the other element by affixing the element directly to the other element, and configurations whereby the element is indirectly secured to the other element by affixing the element to intermediate member(s) which in turn are affixed to the other element.

Figure 1:
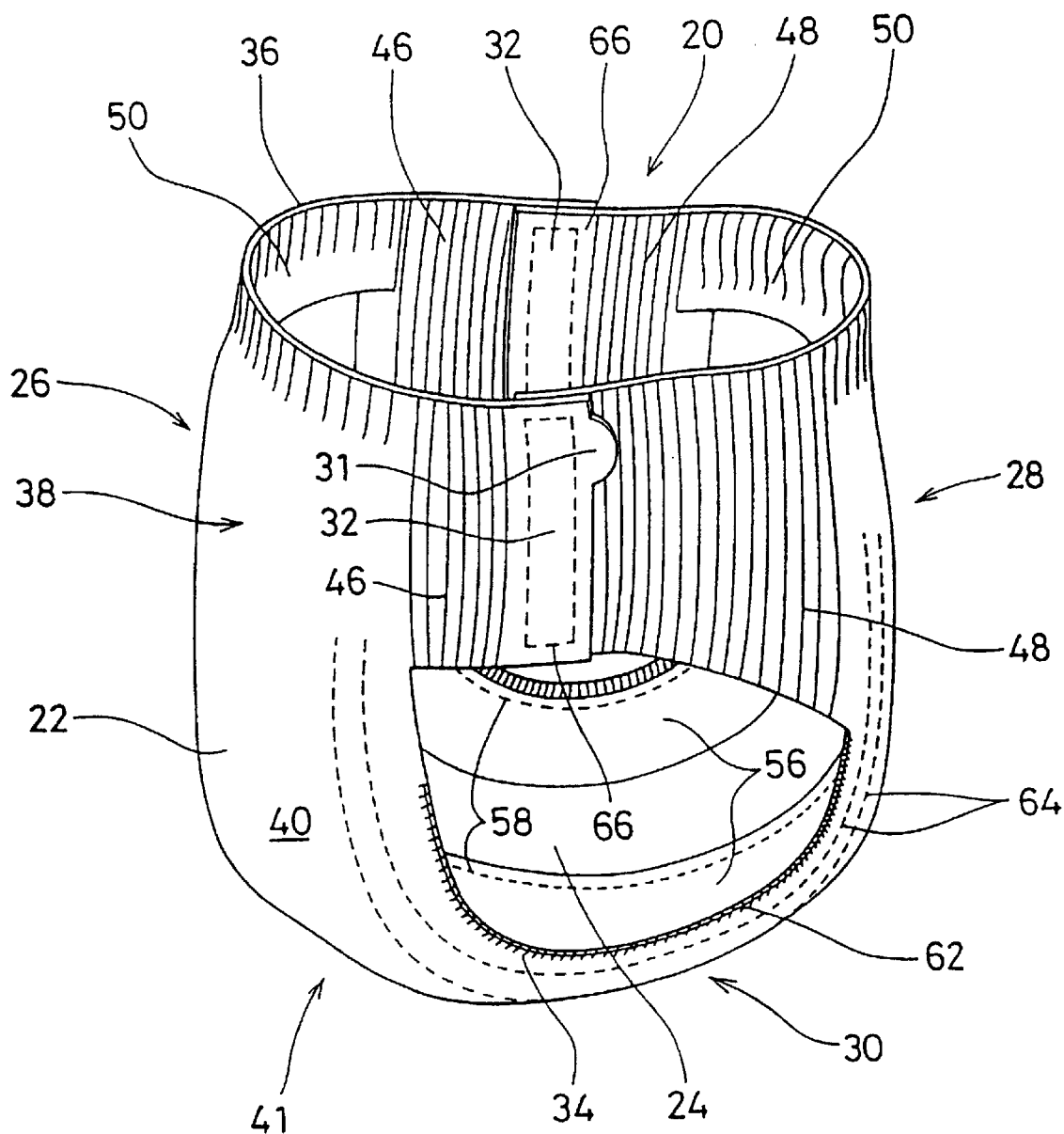
FIG. 1 is a perspective view of a preferred embodiment of the disposable pull-on garment of the present invention in a typical in use configuration.

Referring to FIG. 1, a disposable garment 20 of the present invention comprises a chassis 41 having a front region 26; a back region 28 and a crotch region 30 between the front region 26 and the back region 28; and at least one pair of side panels 46 or 48 extending laterally outwardly from the chassis 41 in the front region 26 or the back region 28. The at least one of the side panels 46 or 48 comprises an elastomeric material 124 (not shown in FIG. 1) extending laterally outwardly from the chassis 41. The chassis 41 comprises a liquid pervious topsheet 24, a liquid impervious backsheet 22 associated with the topsheet 24, and an absorbent core 25 (not shown in FIG. 1) disposed between the topsheet 24 and the backsheet 22.

The backsheet 22 of the invention comprises a liquid impervious film 68. The liquid impervious film 68 of the invention extends in the front, back and crotch regions 26, 28 and 30, and has a nonuniform lateral width LW so as to form a first portion 94 in at least a portion of the crotch region 30, and a second portion 96 in at least a portion of the front or back region 26 and 28. The second portion 96 has a lateral width dimension less than the lateral width dimension of the first portion 94 such that the liquid impervious film 68 does not extend into the at least one pair of side panels (i.e., the front side panels 46 or the back side panels 48). The elastomeric material 124 is joined to the second portion 96 of the liquid impervious film 68. Since the liquid impervious film 68 does not extend into the side panels 46 or 48, the extension properties of the elastomeric material 124 are not affected by the liquid impervious film 68 whereby the side panels 46 or 48 provide an improved fitness to the body of the wearer during use.

Figure 2:
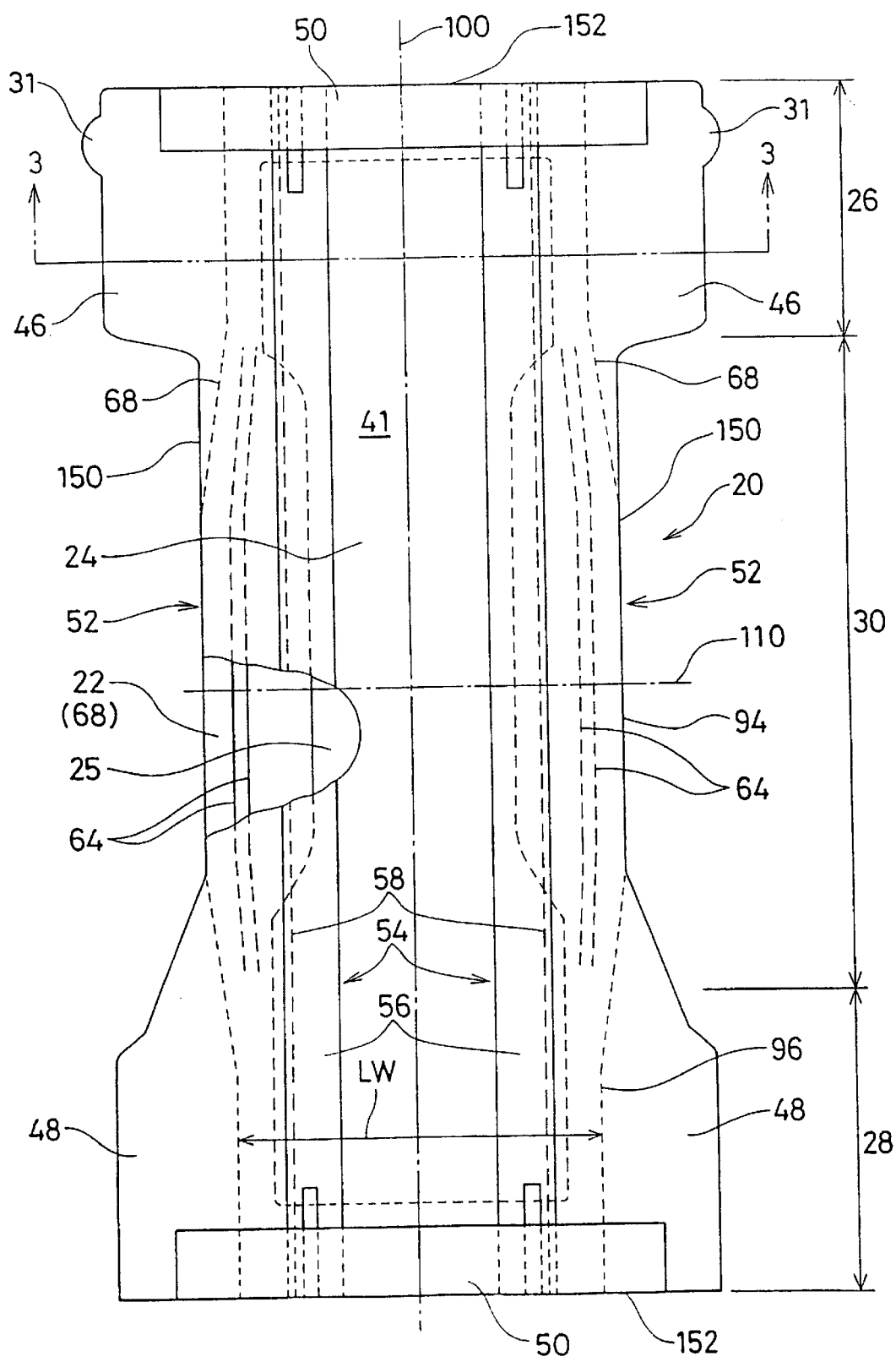
FIG. 2 is a simplified plan view of the embodiment shown in FIG. 1 in its flat uncontracted condition showing the various panels or zones of the garment.

In a preferred embodiment, the lateral width LW of the liquid impervious film 68 gradually decreases towards the waist edge 152, as shown, for example, in FIG. 2 so that the effective lateral length of the elastomeric material 124 can be increased towards the waist edge 152.

The at least one pair of side panels may be either a pair of front side panels 46 or a pair of back side panels 48. In a preferred embodiment wherein the disposable garment 20 is a tape type disposable diaper, the at least one pair of side panels is a pair of the back side panels 48. In an alternative preferred embodiment wherein the disposable garment 20 is a pull-on type disposable diaper, the at least one pair of side panels comprises a pair of front side panels 46 provided in the front region 26 and a pair of back side panels 48 provided in the back region 28, and the disposable garment 20 further comprises seams 32 each joining the corresponding edges of the side panels 46 and 48, thereby forming two leg openings 34 and a waist opening 36.

FIG. 1 shows one preferred embodiment of a disposable garment of the present invention (i.e., a pull-on diaper 20). The pull-on diaper 20 comprises the chassis 41 having the front region 26, the back region 28 and the crotch region 30 between the front region 26 and the back region 28. The chassis 41 comprises the liquid pervious topsheet 24, the liquid impervious backsheet 22 associated with the topsheet 24, and an absorbent core 25 (not shown in FIG. 1 but in FIG. 2) disposed between the topsheet 24 and the backsheet 22. The pull-on diaper 20 further comprises the front side panels 46 each extending laterally outwardly from the corresponding side of the chassis 41 in the front region 26, and back side panels 48 each extending laterally outwardly from the corresponding side of the chassis 41 in the back region 28. Preferably, at least one pair of the front and back side panels 46 and 48 are elastically extensible in at least the lateral direction. The pull-on diaper 20 further comprises seam panels 66 each extending laterally outwardly from each of the front and back side panels 46 and 48; and tear open tabs 31 each extending laterally outwardly from the seam panels 66. Other preferred examples of the pull-on diaper 20 are disclosed in U.S. Pat No. 5,569,234 to Buell et al. on Oct. 29, 1996.

Preferably at least one of, more preferably both of, the pairs of the front and back side panels 46 and 48 is elastically extensible. As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided. The extensible side panels 46 and/or 48 provide a more comfortable and contouring fit by initially conformably fitting the diaper to the wearer and sustaining this fit throughout the time of wear well past when the diaper has been loaded with exudates since the side panels 46 and/or 48 allow the sides of the diaper to expand and contract.

In a preferred embodiment, the front and back side panels 46 and 48 are elastically extensible only in the lateral direction. In an alternative embodiment, the front and back side panels 46 and 48 are elastically extensible both in the lateral and longitudinal directions.

A continuous belt 38 is formed by the front and back side panels 46 and 48, and a part of the chassis 41 about the waist opening 36. Preferably, elasticized waist bands 50 are provided in both the front region 26 and the back region 28. The pull-on diaper 20 additionally comprises elastic leg features 52.

The continuous belt 38 acts to dynamically create fitment forces in the pull-on diaper 20 when positioned on the wearer, to maintain the pull-on diaper 20 on the wearer even when loaded with body exudates thus keeping the absorbent core 25 in close proximity to the wearer, and to distribute the forces dynamically generated during wear about the waist thereby providing supplemental support for the absorbent core 25 without binding or bunching the absorbent core 25.

The front and back side panels 46 and 48 may be formed by unitary elements of the pull-on diaper 20 (i.e., they are not separately manipulative elements secured to the pull-on diaper 20, but rather are formed from and are extensions of one or more of the various layers of the pull-on diaper). In a preferred embodiment, each of the front and back side panels 46 and 48 is a projected member of the chassis 41 (more clearly shown in FIG. 2). Preferably, the front side panels 46 and back side panels 48 comprises at least one unitary element or a continuous sheet material (e.g. the backsheet nonwoven 23 in FIG. 3) that forms a part of the chassis 41 and continuously extends to the front side panels 46 and back side panels 48.

In preferred embodiments, each of the seam panels 66 is an extension of the corresponding front and back side panels 46 and 48, or at least one of the component elements used therein, or any other combination of the elements. Preferably, each of the tear open tabs 31 is also an extension of the corresponding seam panels 66 or at least one of their component elements used therein, or any other combination of the elements.

Alternatively, the front and side panels 46 and 48 may be discrete members (not shown in FIGS.) which do not have any unitary element that forms a part of the chassis 41. The front and side panels are formed by joining the discrete members to the side edges of the chassis 41.

The pull-on diaper 20 further comprises seams 32 each joining the corresponding edges of the front and side panels 46 and 48, thereby forming two leg openings 34 and a waist opening 36. Preferably, the front and side panels 46 and 48 are seamed, more preferably through the seam panels 66, in an overlap manner to make an overlapped seam structure. Alternatively, the front and side panels 46 and 48 can be seamed in a butt seam manner (not shown in FIGS.). The bonding of the seams 32 can be performed by any suitable means known in the art appropriate for the specific materials employed in the front and back side panels 46 and 48. Thus, sonic sealing, heat sealing, pressure bonding, adhesive or cohesive bonding, sewing, autogeneous bonding, and the like may be appropriate techniques. Preferably, the seam panels 66 are joined by a predetermined pattern of heat/pressure or ultrasonic welds which withstands the forces and stresses generated on the diaper 20 during wear.

FIG. 2 is a partially cut-away plan view of the pull-on diaper 20 of FIG. 1 in its flat-out, uncontracted state (i.e., with elastic induced contraction pulled out except in the side panels 46 and 48 which are left in their relaxed condition) with the topsheet 24 facing the viewer, prior to the side panels 46 and 48 are joined together by the seams 32. The pull-on diaper 20 has the front region 26, the back region 28 opposed to the front region 26, the crotch region 30 positioned between the front region 26 and the back region 28, and a periphery which is defined by the outer perimeter or edges of the pull-on diaper 20 in which the side edges are designated 150 and the end edges or waist edges are designated 152. The topsheet 24 has the body-facing surface of the pull-on diaper 20 which is positioned adjacent to the wearer's body during use. The backsheet 22 has the outer-facing surface or the of the pull-on diaper 20 which is positioned away from the wearer's body. The pull-on diaper 20 comprises the chassis 41 comprising the liquid pervious topsheet 24; the liquid impervious backsheet 22 associated with the topsheet 24; and the absorbent core 25 positioned between the topsheet 24 and the backsheet 22. The diaper 20 further comprises the front and back side panels 46 and 48 extending laterally outwardly from the chassis 41; the elasticized leg cuffs 52; and the elasticized waistbands 50. The topsheet 24 and the backsheet 22 have length and width dimensions generally larger than those of the absorbent core 25. The topsheet 24 and the backsheet 22 extend beyond the edges of the absorbent core 25 to thereby form the periphery of the diaper 20. The liquid impervious backsheet 22 preferably comprises a liquid impervious plastic film 68 which is joined to the backsheet nonwoven 23.

While the topsheet 24, the backsheet 22, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The pull-on diaper 20 also has two centerlines, a longitudinal centerline 100 and a transverse centerline 110. The term "longitudinal", as used herein, refers to a line, axis, or direction in the plane of the pull-on diaper 20 that is generally aligned with (e.g. approximately parallel with) a vertical plane which bisects a standing wearer into left and right halves when the pull-on diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves). The pull-on diaper 20 and component materials thereof also have a body-facing surface which faces the skin of wearer in use and an outer-facing surface which is the opposite surface to the body-facing surface.

Figure 3:
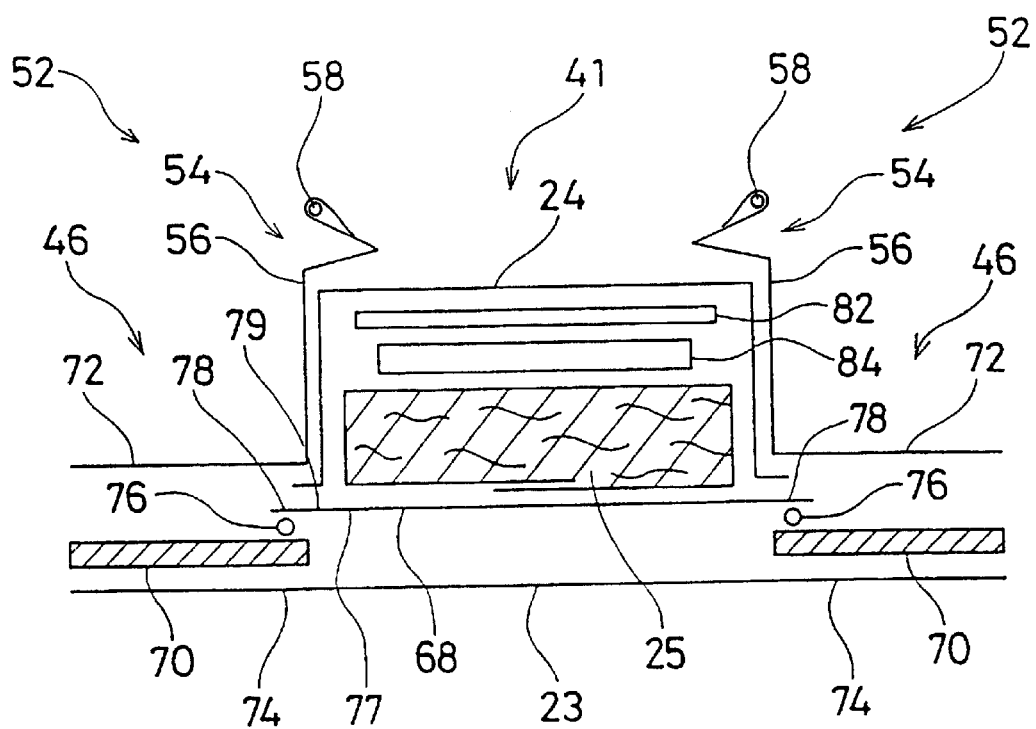
FIG. 3 is a cross-sectional view of a preferred embodiment taken along the section line 3—3 of FIG. 2.

FIG. 3 is a cross-sectional view of a preferred embodiment taken along the section line 3—3 of FIG. 2. The pull-on diaper 20 comprises the chassis 41 comprising the liquid pervious topsheet 24; the liquid-impervious backsheet 22 associated with the topsheet 24; and the absorbent core 25 positioned between the topsheet 24 and the backsheet 22. The diaper further comprises the front side panels 46 each extending laterally outwardly from the chassis 41; and the elasticized leg cuffs 52. although FIG. 3 depicts only the structure of the front side panel 46, preferably the back side panels 48 have the similar structures. Preferably, the chassis 41 further comprises an acquisition/distribution layer 82 and/or an acquisition/distribution core 84 between the topsheet 24 and the absorbent core 25. Each of the front side panels 46 is formed by the lamination of an extended part 72 of the barrier flap 56, an elastic member 70 and the backsheet nonwoven 74.

The absorbent core 25 may be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may comprise one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the diaper 20.

A preferred embodiment of the diaper 20 has an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat No. 4,673,402 entitled "Absorbent Articles With Dual-Layered Cores" issued to Weisman et al. on Jun. 16, 1987; U.S. Pat No. 4,888,231 entitled "Absorbent Core Having A Dusting Layer" issued to Angstadt on Dec. 19, 1989; and U.S. Pat No. 4,834,735, entitled "High Density Absorbent Members Having Lower Density and Lower Basis Weight Acquisition Zones", issued to Alemany et al. on May 30, 1989.

The chassis 41 may further comprise an acquisition/distribution core 84 of chemically stiffened fibers positioned over the absorbent core 25, thereby forming a dual core system. Preferred dual core systems are disclosed in U.S. Pat No. 5,234,423, entitled "Absorbent Article With Elastic Waist Feature and Enhanced Absorbency" issued to Alemany et al., on Aug. 10, 1993; and in U.S. Pat No. 5,147,345, entitled "High Efficiency Absorbent Articles For Incontinence Management" issued to Young, LaVon and Taylor on Sep. 15, 1992. In a preferred embodiment, the acquisition/distribution core 84 comprise chemically treated stiffened cellulosic fiber material, available from Weyerhaeuser Co. (U.S.A.) under the trade designation of CMC.

More preferably, the chassis 22 further comprises an acquisition/distribution layer 82 between the topsheet 24 and the acquisition/distribution core 84 as shown in FIG. 3. The acquisition/distribution layer 82 is provided to help reduce the tendency for surface wetness of the topsheet 24. The acquisition/distribution layer 82 preferably comprises carded, resin bonded hiloft nonwoven materials such as, for example, available as Code No. FT-6860 from Polymer Group, Inc., North America (Landisiville, N.J., U.S.A.), which is made of polyethylene telephthalate fibers of 6 dtex, and has a basis weight of about 43 g/m$^2$.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 10 24 rather than being drawn through the topsheet 24 and being absorbed by the absorbent core 25. The topsheet 24 can be rendered hydrophilic by treating it with a surfactant. Suitable methods for treating the topsheet 24 with a surfactant include the topsheet 24 material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

In preferred embodiments, the topsheet 24 is a nonwoven web that can provide reduced tendency for surface wetness; and consequently facilitate maintaining urine absorbed by the core 25 away from the user's skin, after wetting. One of the preferred topsheet materials is a thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded carded web which is available as Code No. Profleece Style 040018007 from Amoco Fabrics, Inc. (Gronau, Germany).

Another preferred topsheet 24 comprises an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991.

In preferred embodiments, the backsheet 22 comprises the liquid impervious film 68 as shown in, for example, FIG. 3. The liquid impervious film 68 has a body-facing surface 79 and an outer-facing surface 77. The liquid impervious film 68 is preferably impervious to liquids (e.g., urine) and is preferably manufactured from a thin plastic film. However, more preferably the plastic film permits vapors to escape from the diaper 20. In a preferred embodiment, a microporous polyethylene film is used for the plastic film 68. A suitable microporous polyethylene film is manufactured by Mitsui Toatsu Chemicals, Inc., Nagoya, Japan and marketed in the trade as Espoir No.

A suitable material for the plastic film 68 is a thermoplastic film having a thickness of from about 0.012 mm (0.5 mil) to about 0.051 mm (2.0 mils), preferably comprising polyethylene or polypropylene. Preferably, the plastic film has a basis weight of from about 5 g/m$^2$ to about 35 g/m$^2$. However, it should be noted that other flexible liquid impervious materials may be used. As used herein, the term "flexible" refers to materials which are compliant and which will readily conform to the general shape and contours of the wearers body.

Preferably, the backsheet 22 further comprises a nonwoven outer cover 23 which is joined with the outer-facing surface of the plastic film 68 to form a laminate (i.e., the backsheet 22). The nonwoven outer cover 23 is positioned at the outermost portion of the diaper 20 and covers at least a portion of the outermost portion of the diaper 20. In a preferred embodiment, the nonwoven outer cover 23 covers almost all of the area of the outermost portion of the diaper 20. The nonwoven outer cover 23 may be joined to the plastic film 68 by any suitable attachment means known in the art. For example, the nonwoven outer cover 23 may be secured to the plastic film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

In a preferred embodiment, the nonwoven outer cover 23 is a carded nonwoven web, for example, obtainable from Havix Co., LTD., Gifu, Japan as E-2341. The nonwoven outer cover 23 is made of bi-component fibers of a polyethylene (PE) and a polyethylene terephthalate (PET). The ratio of PE/PET is about 40/60. The PE/PET bi-component fiber has the dimension of 2d×51 mm. Another preferred carded nonwoven web is obtainable from Chisso Corp., Osaka, Japan. The nonwoven outer cover 23 is also made of bi-component fibers of a polyethylene (PE) and a polyethylene terephthalate (PET). The ratio of PE/PET is about 30/70.

In another preferred embodiment, the nonwoven web is a spunbonded nonwoven web, for example, obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PEIPP bi-component fiber has the thickness is approximately 2.3d.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The pull-on diaper 20 preferably further comprises elasticized leg cuffs 52 for providing improved containment of liquids and other body exudates. The elasticized leg cuffs 52 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakageguard gutters configured to contain free liquids within the garment.

While each elasticized leg cuff 52 may be configured so as to be similar to any of the leg bands, side flaps, barrier cuffs, or elastic cuffs described above, it is preferred that each elasticized leg cuff 52 comprises inner barrier cuffs 54 each comprising a barrier flap 56 and a spacing means 58 (as shown in FIGS. 1 and 2) as described in the above-referenced U.S. Pat No. 4,909,803. In a preferred embodiment, the elasticized leg cuff 52 additionally comprises an elastic gasketing cuff 62 with one or more elastic strands 64 (as shown in FIG. 2), positioned outboard of the barrier cuff 54 such as described in the above-referred U.S. Pat. Nos. 4,695,278 and 4,795,454.

The pull-on diaper 20 preferably further comprises an elasticized waistband 50 that provides improved fit and containment. The elasticized waistband 50 is that portion or zone of the pull-on diaper 20 which is intended to elastically expand and contract to dynamically fit the wearer's waist. The elasticized waistband 50 preferably extends longitudinally outwardly from at least one of the waist edges of the absorbent core 25 and generally forms at least a portion of the end edge of the pull-on diaper 20. Preferably, the pull-on diaper 20 has two elasticized waistbands 50, one positioned in the back region 28 and one positioned in the front region 26, although other pull-on diapers can be constructed with a single elasticized waistband. The elasticized waistband 50 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell.

The waistbands 50 may comprise materials that have been "prestrained", or "mechanically prestrained" (i.e., subjected to some degree of localized pattern mechanical stretching to permanently elongate the material. The materials may be prestrained using deep embossing techniques as are known in the art. Alternatively, the materials may be prestrained by directing the material through an incremental mechanical stretching system as described in U.S. Pat No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat No. 2,075,189 issued to Galligan on Mar. 30, 1937; U.S. Pat No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat No. 4,834,741 issued to Sabee on May 30, 1989; and U.S. Pat No. 5,151,092 issued to Buell et al., on Sep. 29, 1992.

Referring to FIG. 3, at least one of the front and back side panels (i.e., the front side panels 46 in this embodiment) comprises the elastic member 70. The elastic member 70 comprises the elastomeric material 124 which preferably extends laterally outwardly from the chassis 41 to provide a good fitness by generating the optimal retention (or sustained) force at the waist area of the wearer. Preferably, the elastomeric material 124 is extensible in at least one direction, preferably in a direction having a vector component in the lateral direction to generate a retention (or sustained) force that is optimal to prevent the pull-on diaper 20 from drooping, sagging, or sliding down from its position on the torso without causing the red marking on the skin of the wearer. In preferred embodiments, both of the front and back side panels 46 and 48 comprise the elastomeric material 124.

The elastic member 70 comprising the elastomeric material 124 (not shown in FIG. 3) is operatively joined to at least one of the nonwoven webs 72 and 74 in the front and back side panels 46 and 48 to allow the elastic member 70 to be elastically extensible in at least the lateral direction. In a preferred embodiment, the elastic member 70 is operatively joined to the nonwoven webs 72 and 74 by securing them to at least one, preferably both of the nonwoven webs 72 and 74 while in a substantially untensioned (zero strain) condition.

The elastic member 70 can be operatively joined to the nonwoven webs 72 and 74, by using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. Because it is preferred that the stretch laminate be bonded over all or a significant portion of the stretch laminate so that the inelastic webs (i.e., the nonwoven webs 72 and 74) elongate or draw without causing rupture, and the layers of the stretch laminates are preferably bonded in a configuration that maintains all of the layers of the stretch laminate in relatively close adherence to one another after the incremental mechanical stretching operation, the elastic panel members and the other plies of the stretch laminate are substantially continuously bonded together using an adhesive. In a particularly preferred embodiment, the adhesive selected is applied in a spiral pattern (such as is shown in U.S. Pat. No. 3,911,173 (Sprague, Jr.) and U.S. Pat. No. 4,842,666 (Werenicz)) at a basis weight of about 0.00116 grams/square cm (0.0075 grams/square inch). The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

After the elastic member 70 is operatively joined to at least one of the nonwoven webs 72 and 74, at least a portion of the resultant composite stretch laminate is then subjected to mechanical stretching sufficient to permanently elongate the non-elastic components which are, for example, the nonwoven webs 72 and 74. The composite stretch laminate is then allowed to return to its substantially untensioned condition. At least one pair of, preferably both of the front and back side panels 46 and 48 is thus formed into "zero strain" stretch laminates. (Alternatively, the elastic member 70 could be operatively joined in a tensioned condition and then subjected to mechanical stretching; although this is not as preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat No. 5,156,793 issued to Buell et al. on Oct. 20, 1990; and U.S. Pat No. 5,143,679 issued to Weber et al. on Sep. 1, 1992. It should be noted that the Japanese equivalent applications to these U.S. Patents were published (laid open) in Japanese under the Nos. of H6-505681, H6-505408 and H6-505446, respectively.

The elastic member 70 is preferably joined to, more preferably directly secured to the respective edges 78 of the liquid impervious film (i.e., the plastic film 68) though an adhesive 76 as shown in FIG. 3. In a preferred embodiment, the elastic member 70 is joined to the respective edges 78 of the plastic film 68 at the outer-facing surface 77 as shown in FIG. 3. In an alternative embodiment, the elastic member 70 may be joined to the respective edges 78 of the plastic film 68 at the body-facing surface 79 (not shown in FIGS.). Preferably, the adhesive 76 is applied as an bead. In preferred embodiments, the adhesive 76 is a flexible adhesive with an amorphous and crystallizing component. Such a preferred adhesive is made by the Findley Adhesive Company under the designation H9224. Alternatively, the elastic member 70 may be joined to the respective edges 78 of the plastic film 68 by any other bonding means known in the art which comprise heat bonds, pressure bonds, ultrasonic bonds, dynamic mechanical bonds, or combinations of these attachment means.

Figure 4:
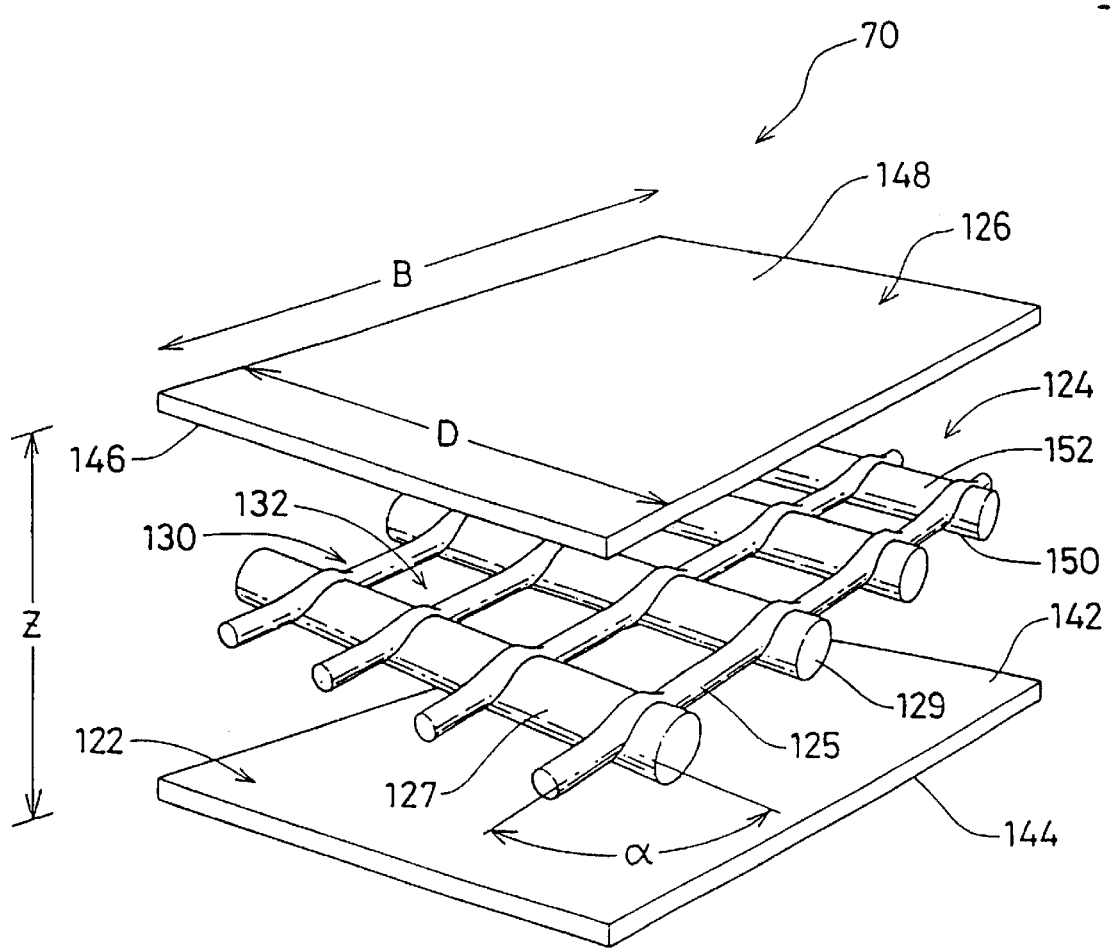
FIG. 4 is a cross-sectional view of an elastic member 70 of a preferred embodiment.

Referring to FIG. 4, the elastic member 70 comprises the elastomeric material 124 having a first surface 150 and a second surface 152 opposing the first surface 150, and a first coverstock layer 122 which is joined to the first surface 150 of the elastomeric material 124. In a preferred embodiment, the first coverstock layer 122 is joined to the first surface 150 of the elastomeric material 124 by an adhesive 160 as shown, for example, in FIG. 5. More preferably, the elastic member 70 further comprises a second coverstock layer 126 which is joined to the second surface 152 of the elastomeric material 124 by an adhesive 164.

Preferably, the elastic member 70 is joined to the respective edges 78 of the plastic film 68 at the outer-facing surface 77 as shown in FIG. 3. In an alternative embodiment, the elastic member 70 may be joined to the respective edges 78 of the plastic film 68 at the body-facing surface 79 (not shown in FIGS.).

The elastomeric material 124 may be formed in a wide variety of sizes, forms and shapes. In a preferred embodiment, the elastomeric material 124 is in the form of a continuous plane layer. Preferred forms of continuous plane layer include a scrim, a perforated (or apertures formed) film, an elastomeric woven or nonwoven, and the like. In an alternative embodiment, the elastomeric material 124 is in the form of strands (or strings) which are not connected each other to form a continuous plane layer. The continuous plane layer may take any shape which can be suitably provided in the side panels. Preferred shapes of continuous plane layer include a quadrilateral including a rectangle and a square, a trapezoid, and the other polygons.

Elastomeric materials which have been found to be especially suitable for the elastomeric material 124 are styrenic block copolymer based scrim materials, perforated (or apertured) elastic films, preferably with a thickness of from about 0.05 mm to about 1.0 mm (0.002 inch–0.039 inch). Other suitable elastomeric materials for the elastomeric material 124 include "live" synthetic or natural rubber, other synthetic or natural rubber foams, elastomeric films (including heat shrinkable elastomeric films), elastomeric woven or nonwoven webs, elastomeric composites, or the like.

The extension properties of the elastomeric material 124 such as the First Cycle Extension Force at 100% Extension (FCEF100%), the First Cycle Extension Force at 200% Extension (FCEF200%), and the Second Cycle Recovery Force at 50% Extension (SCRF50%) are important considerations in the performance of disposable garments. The elastomeric material 124 preferably has extension properties within the defined ranges herein. The FCEF100% and the FCEF200% are measures of the overall perceived "stretchness" during application/removing of disposable garments. These two properties also effect the ability of the applicator to achieve a suitable degree of application stretch. An elastomeric material 124 with a relatively high FCEF100% and FCEF200% can causes difficulty in applying the disposable garment onto the wearer (i.e., ease of application problem). On the other hand, an elastomeric material 124 with a relatively low FCEF100% and FCEF200% may not achieve a suitable level of body fitting/conformity. The SCRF50% also closely relates to the body fitting/conformity of disposable garments for the wearer. An elastomeric material 124 with a relatively high SCRF50% tends to cause red marking on the skin of the wearer and may be uncomfortable for the wearer during usage. An elastomeric material 124 with a relatively low SCRF50% may not provide enough elastic force to keep the diaper in place on the wearer or may not provide good body fit.

The values of FCEF100%, FCEF200% and SCRF50% can be measured by using a tensile tester. The tensile tester comprises an upper jaw and a lower jaw which is located below the upper jaw. The upper jaw is movable and is connected to an extension force measuring means. The lower jaw is fixed at a desk (or floor). A test specimen (i.e., the elastomeric material to be measured) which has about 2.54 cm (1.0 inch) in width and about 12.75 cm (5 inches) in length is prepared and clamped between the upper jaw and the lower jaw so that the effective specimen length (L) (i.e., gauge length) is about 5.08 cm (2.0 inches). The extension force is applied to the test specimen through the upper jaw. When no extension force is applied to the test specimen, the test specimen is in its original length (i.e., 0% extension). A tensile tester suitable for use herein is available from Instron Corporation (100 Royall Street, Canton, MA02021, U.S.A.) as Code No. Instron 5564.

Figure 6:
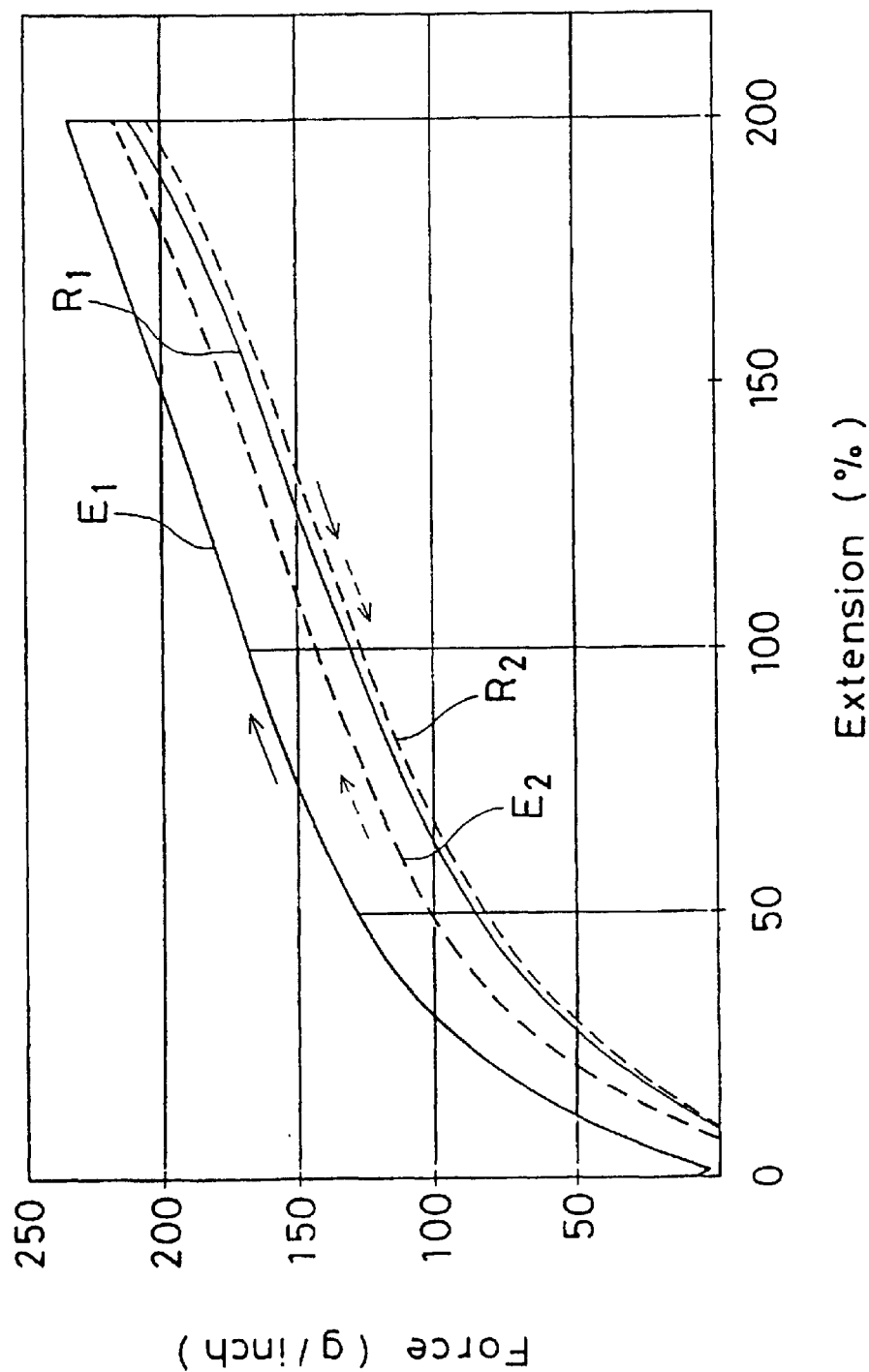
FIG. 6 is a graph showing the two-cycles of hysteresis curves of an elastomeric material, in a preferred embodiment.

FIG. 6 shows one preferred example of the extension and recovery force curves for the two cycle hysteresis of the elastomeric material 124. The curve E1 shows the extension force in the first cycle, while the curve R1 shows the recovery force in the first cycle. The curve E2 (shown in dashed lines) shows the extension force in the second cycle, while the curve R2 shows the recovery force in the second cycle. The extension and recovery properties are measured as follows.

In the first cycle, the test specimen is subjected to an initial extension force at a crosshead rate of 50.8 cm/min (20 in/min) at about 23° C. and held for 30 seconds at 200% extension. The test specimen is then allowed to relax at the same rate to the original state (i.e., 0% extension). The test specimen is allowed to remain unconstrained for one minute before being subjected to a second extension force (for the second cycle) at the same rate and conditions.

In preferred embodiments, the FCEF100% of the elastomeric material 124 is at least about 100 grams/inch. More preferably, the FCEF100% is between about 120 to about 220 grams/inch, most preferably between about 150 grams/inch and 190 grams/inch to best fit the wearer. The FCEF200% is preferably between about 160 grams/inch and about 320 grams/inch, more preferably between about 180 grams/inch and about 260 grams/inch, and yet more preferably between about 200 grams/inch and about 240 grams/inch.

The SCRF50% of the elastomeric material 124 is preferably between about 40 grams/inch and about 130 grams/inch, more preferably between about 65 grams/inch and about 105 grams/inch, and yet more preferably between about 75 grams/inch and about 95 grams/inch.

In the preferred embodiment shown in FIG. 4, the elastomeric scrim 124 has a plurality of first strands 125 and a plurality of second strands 127. The plurality of first strands 125 intersect the plurality of second strands 127 at nodes 130 at a predetermined angle α, forming a net-like open structure having a plurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. Preferably, the first and second strands 125 and 127 are substantially straight and substantially parallel to one another. Preferably, the first strands 125 intersect the second strands 127 at nodes 130 such that the angle α is about 90 degrees. The first and second strands 125 and 127 are preferably joined or bonded at nodes 90.

A preferred elastomeric scrim 124 is manufactured by the Conwed Plastics Company under the designation XO2514. This material has about 12 elastic strands per inch in the structural direction B (i.e., the first strands 125) and about 7 elastic strands per inch in the structural direction D (i.e., the second strands 127).

In the embodiment shown in FIG. 4, the elastic member 70 comprises first and second coverstock layers 122 and 126, and elastomeric material 124 disposed in the first and second coverstock layers 122 and 126. The first coverstock layer 122 has an inner surface 142 and an outer surface 144. The inner surface 142 of the first coverstock layer 122 is the surface that is positioned facing the elastomeric material 124. The second coverstock layer 126 also has an inner surface 146 and an outer surface 148. The inner surface 146 of the second coverstock layer 126 is the surface that is positioned facing the elastomeric material 124. The elastomeric material 124 also has two planar surfaces, first surface 150 and second surface 152, each of which is substantially parallel with the planes of the first and second coverstock layers 122 and 126. The first surface 150 is that planar surface of the elastomeric material 124 that is most closely adjacent with the inner surface 142 of first coverstock layer 122. The second surface 152 is that planar surface of elastomeric material 124 that is most closely adjacent to the inner surface 146 of the second coverstock layer 126.

Since the elastic member 70 will be subjected to mechanical stretching before and during use, the first and second coverstock layers 122 and 126 preferably has a relatively high elongation at breaking, and are more preferably stretchable or elongatable, yet more preferably drawable (but not necessarily elastomeric), without undue and preferably without any, tearing or ripping. Further, the first and second coverstock layers 122 and 126 are preferably compliant, soft feeling, and non-irritating to the wearer's skin and give the article the feel and comfort of a cloth garment. Suitable materials for the first and second coverstock layers 122 and 126 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Preferably, each of the first and second coverstock layers 122 and 126 is an identical consolidated nonwoven material. An exemplary preferred nonwoven material is manufactured by the FiberWeb Company under the designation Sofspan 200. This material has a basis weight of 25 g/m² before consolidation and a basis weight of about 63 g/m2 after consolidation. As used herein, "basis weight" is the weight of one square meter of planar web material. Alternatively, highly strainable nonwoven materials may be used. Alternatively, the first and second coverstock layers 122 and 126 need not be of identical materials, as long as the desired performance requirements, such as elastic performance, softness, flexibility, breathability and durability, are met. As used herein, "consolidated nonwoven material" means a nonwoven material that has been gathered or necked under mechanical tension in the structural direction D so that the material can elongate in the structural direction D under low force.

Figure 5:
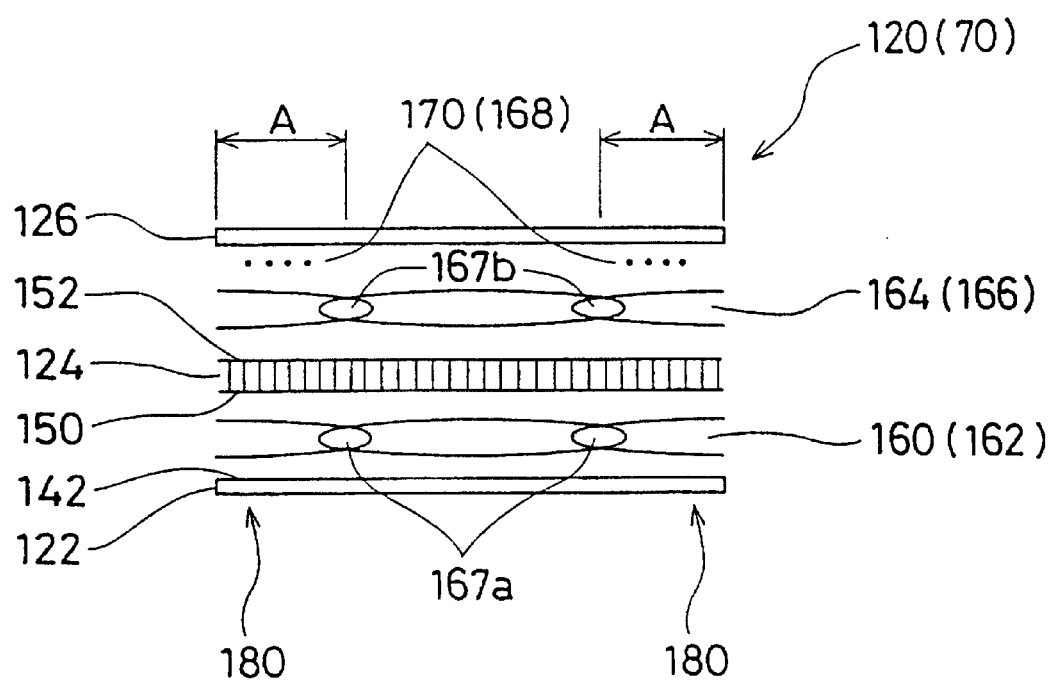
FIG. 5 is a fragmentary enlarged side view of the elastic member 70 shown in FIG.4.

FIG. 5 shows a fragmentary enlarged side view looking into the structural direction B of the laminate 120 (i.e., the elastic member 70). It has been found that when the laminate 120 is bonded or otherwise anchored such that side anchor zones A are created, such a laminate 120 is both highly elastic and substantially free from delamination and creep, while providing very good performance characteristics in all performance categories with no trade-offs between any performance characteristics required. The side anchoring is preferably performed by side gluing with adhesive beads to anchor the elastomeric material 124 between the coverstock layers 122 and 126 as a part of the lamination process. Alternatively, side anchoring may be performed by sewing, heat sealing, ultrasound bonding, needle punching, alternative gluing processes, or by any other means known to those skilled in the art. Another alternative is to side anchor the layers of the laminate structure after the lamination of the elastomeric and coverstock components has been performed.

Preferably, the laminate 120 may particularly provide very good soft feel for the wearer and for the consumer. This is important because consumers value softness. In conventional laminates, the attempts to eliminate creep have frequently required an unacceptable decrease in softness, often accompanied by an unacceptable decrease in the ability to activate. This is because such previous attempts (which have fallen short of eliminating creep) have focused on the application of additional melt blown adhesive, often in an overall coating pattern in the attempt to strengthen the bonds. This has generally resulted in an undesirable overall stiffening of the laminate. However, the laminates of the preferred embodiments provide elimination of creep without the loss of consumer-desired soft feel and without compromise of activation ability.

Referring to FIG. 5, a first adhesive 170 is applied to the inner surface 146 of the second coverstock layer 126 in positions that correspond to each of the outer edges 180 of the laminate structure 120. The first adhesive 170 may alternatively or additionally be applied to the inner surface 142 of the first coverstock layer 122. For ease of illustration, the description and FIGS. refer to application to the second coverstock layer 126 only.

This pattern creates side anchor zones A, which substantially eliminate the delamination and creep associated with previously known laminates and which allows the laminate 120 to experience higher strains without creeping or delaminating. It has also been found that confining the first adhesive 170 to the edge areas 180 of the laminate structure 120 avoids impeding the extensibility of the laminate 120 and also avoids tears in the coverstock layers 122 and 126. Preferably, the first adhesive 170 is applied as a plurality of beads 168, as shown in FIG. 5. Preferably, the first adhesive 170 is a flexible adhesive with an amorphous and crystallizing component. Such a preferred adhesive is made by the Findley Adhesive Company under the designation H9224.

More preferably, the laminate 120 includes a second adhesive 164. The second adhesive 164 is preferably applied to the second surface 152 of the elastomeric material 124, but could alternatively be applied to the first surface 150 of the elastomeric material 24. The second adhesive 164 is preferably applied in a spiral spray pattern 166, thereby forming bond points 167b that are more discrete than would be formed by a linear spray application. Without being bound by theory, it is believed that most of the second adhesive 164 so sprayed aligns in the structural direction D. Thus, it has been found that spiral spraying results in very good activation properties. As used herein, "activation" refers to the ability to stretch.

It has been found that spraying the layer of second adhesive 164 directly onto the second surface 152 of the elastomeric material 124 is more preferable than applying the second adhesive 164 to the opposing (i.e., second) coverstock layer 126. This is because the second adhesive 164 tends to penetrate through any residual processing agents or oils that may remain on the surface of the elastomeric material 124. Such residual materials, if left to remain on the elastomeric material 124, may weaken the adhesive bonds and thus the laminate structure 120 over time. For example, if these residual materials are left intact, the bonds used to form the laminate 120 may weaken during the time interval prior to consumer purchase of the product.

Peel values for the laminate 120 in the spiral adhesive areas are typically higher when the spirals 166 are applied directly to the elastomeric material 124 than to the opposing (i.e., second) coverstock layer 126. As used herein, the term "peel value" refers to the amount of force required to separate the two layers of coverstock material, 122 and 126, from each other. Higher peel values typically equate to less chance of delamination in use.

A third adhesive 160 may also preferably be applied to the inner surface 142 of the first coverstock layer 122. Preferably, the third adhesive 160 is an elastomeric adhesive. In a manner similar to that described with reference to the second spiral adhesive application 166, the first adhesive 160 is preferably applied in a spiral spray pattern 162, thereby forming bond points 167a that are more discrete than would be formed by a linear spray application. Without being bound by theory, it is believed that most of the first adhesive 160 so sprayed aligns in the structural direction D.

Preferably, second and third adhesives 160 and 164 are the same elastomeric adhesive. A preferred adhesive for use in the second and third adhesive spiral sprays 162 and 166 is made by the Findley Adhesive Company under the designation H2120. Preferably, the add-on level for each of the second and third spiral sprays 162 and 166 is about 4 to about 12 milligrams per square inch, more preferably about 8 milligrams per square inch.

It is understood that the examples and embodiments described herein are for illustrative purpose only and that various modifications or changes will be skilled in the art without departing from the scope of the present invention.

What is claimed is:

1. A disposable garment, comprising:
   a chassis having a front region, a back region and a crotch region between the front region and back region, the chassis comprising a liquid pervious topsheet, a liquid impervious backsheet associated with the topsheet, and an absorbent core disposed between the topsheet and the backsheet; and
   at least one pair of side panels extending laterally outwardly from the chassis in the front or back region;
   the backsheet comprising a liquid impervious film having a body-facing surface and extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;
   at least one of the side panels comprising an elastomeric material extending laterally outwardly from the chassis;
   wherein the elastomeric material is joined to the second portion of the liquid impervious film at the body-facing surface.

2. The disposable garment according to claim 1, wherein the lateral width of the liquid impervious film gradually decreases towards the waist edge.

3. A disposable garment, comprising:
   a chassis having a front region, a back region and a crotch region between the front region and back region, the chassis comprising a liquid pervious topsheet, a liquid impervious backsheet associated with the topsheet, and an absorbent core disposed between the topsheet and the backsheet; and
   at least one pair of side panels extending laterally outwardly from the chassis in the front or back region;
   the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;
   at least one of the side panels comprising an elastomeric material extending laterally outwardly from the chassis and joined to the second portion of the liquid impervious film;
   wherein the at least one pair of side panels is a pair of back side panels provided in the back region.

4. A disposable garment, comprising:
   a chassis having a front region, a back region and a crotch region between the front region and back region, the chassis comprising a liquid pervious topsheet, a liquid impervious backsheet associated with the topsheet, and an absorbent core disposed between the topsheet and the backsheet; and
   at least one pair of side panels extending laterally outwardly from the chassis in the front or back region;
   the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;
   at least one of the side panels comprising an elastomeric material extending laterally outwardly from the chassis and Joined to the second portion of the liquid impervious film;
   wherein the at least one of the side panels is formed from a "zero strain" stretch laminate.

5. A disposable garment, comprising:
   a chassis having a front region, a back region and a crotch region between the front region and back region, the chassis comprising a liquid pervious topsheet, a liquid impervious backsheet associated with the topsheet, and an absorbent core disposed between the topsheet and the backsheet; and
   at least one pair of side panels extending laterally outwardly from the chassis in the front or back region;

the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;

at least one of the side panels comprising an elastomeric material extending laterally outwardly from the chassis and joined to the second portion of the liquid impervious film;

wherein the at least one pair of side panels comprises a pair of front side panels provided in the front region and a pair of back side panels provided in the back region, and the disposable garment further comprises seams each joining the corresponding edges of the side panels, thereby forming two leg openings and a waist opening.

6. The disposable garment according to claim 5, wherein the corresponding front and back side panels are seamed in an overlap manner to make an overlapped seam structure.

7. A disposable garment, comprising:

a chassis having a front region, a back region and a crotch region between the front region and back region, the chassis comprising a liquid pervious topsheet, a liquid impervious backsheet associated with the topsheet, and an absorbent core disposed between the topsheet and the backsheet; and at least one pair of side panels extending laterally outwardly from the chassis in the front or back region;

the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;

at least one of the side panels comprising an elastomeric material extending laterally outwardly from the chassis and joined to the second portion of the liquid impervious film;

wherein the backsheet further comprises a nonwoven outer cover joined to the liquid impervious film.

8. A disposable garment, comprising:

a chassis having a front region, a back region and a crotch region between the front region and back region, the chassis comprising a liquid pervious topsheet, a liquid impervious backsheet associated with the topsheet, and an absorbent core disposed between the topsheet and the backsheet; and at least one pair of side panels extending laterally outwardly from the chassis in the front or back region;

the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;

at least one of the side panels comprising an elastomeric material extending laterally outwardly from the chassis and joined to the second portion of the liquid impervious film;

wherein the elastomeric material is an elastomeric scrim.

9. A disposable garment, comprising:

a chassis having a front region, a back region and a crotch region between the front region and back region, the chassis comprising a liquid pervious topsheet, a liquid impervious backsheet associated with the topsheet, and an absorbent core disposed between the topsheet and the backsheet; and at least one pair of side panels extending laterally outwardly from the chassis in the front or back region;

the backsheet comprising a liquid impervious film extending longitudinally in the front, back and crotch regions, the liquid impervious film having a nonuniform lateral width so as to form a first portion in at least a portion of the crotch region, and a second portion in at least a portion of the front or back region, the second portion having a lateral width dimension less than the lateral width dimension of the first portion when the garment is in a flat uncontracted condition such that the film does not extend into the at least one pair of side panels;

at least one of the side panels comprising an elastomeric material extending laterally outwardly from the chassis and joined to the second portion of the liquid impervious film;

wherein the elastomeric material is a perforated film.

* * * * *

UNITED STATES PATENT AND TRADEMARK OFFICE
CERTIFICATE OF CORRECTION

PATENT NO. : 6,582,414 B1
DATED : June 24, 2003
INVENTOR(S) : James William Richardson It is certified that error appears in the above-identified patent and that said Letters Patent is hereby corrected as shown below:

Column 1,
Line 35, delete "1gaue" and insert therefor -- Igaue --.

Column 2,
Line 27, delete "better a understood" and insert therefor -- better understood --.

Signed and Sealed this

Twenty-seventh Day of July, 2004

JON W. DUDAS
*Acting Director of the United States Patent and Trademark Office*